US006847442B1

United States Patent
Katzir et al.

(10) Patent No.: US 6,847,442 B1
(45) Date of Patent: Jan. 25, 2005

(54) ILLUMINATOR FOR INSPECTING SUBSTANTIALLY FLAT SURFACES

(75) Inventors: Yigal Katzir, Rishon-Lezion (IL); Eyal Teichman, Hod-Hasharon (IL); Idit Wechsler, Holon (IL); Shabtai Negry, Givat-Shmuel (IL); Avraham Gross, Ramat-Aviv (IL); Oded Arnon, Givatayim (IL)

(73) Assignee: Orbotech, Ltd., Yavne (IL)

( * ) Notice: Subject to any disclaimer, the term of this patent is extended or adjusted under 35 U.S.C. 154(b) by 0 days.

(21) Appl. No.: 09/719,728

(22) PCT Filed: Jun. 16, 1998

(86) PCT No.: PCT/IL98/00285

§ 371 (c)(1),
(2), (4) Date: Dec. 13, 2000

(87) PCT Pub. No.: WO99/66314

PCT Pub. Date: Dec. 23, 1999

(51) Int. Cl.$^7$ .............................................. G01N 21/00
(52) U.S. Cl. ................... 356/237.2; 356/237.5
(58) Field of Search ............................ 356/237.1–237.5, 356/394, 239.1, 429–432, 445–448; 250/559.4, 559.45

(56) References Cited

U.S. PATENT DOCUMENTS

| 804,996 A | 11/1905 | Anthony ..................... 350/537 |
| 2,257,881 A | 10/1941 | Jaros ............................ 240/1 |
| 2,852,693 A | 9/1958 | Hughes et al. ................ 250/71 |

(List continued on next page.)

FOREIGN PATENT DOCUMENTS

| DE | 36 26 446 | 2/1988 |
| DE | 37 21 114 | 5/1988 |
| EP | 0 116 321 A | 8/1984 |
| EP | 0 196 789 A | 10/1986 |
| JP | 57-19712 A | 2/1982 |
| JP | 59-123980 A | 7/1984 |

OTHER PUBLICATIONS

LaMuth, "Measurements on Lambertain Objects: Some Novel Approaches", Applied Optics, vol. 14, No. 5, May 1975, pp. 1150–1155.
Advertisement, "High Irradiance Reflectors", Vortek Industries Ltd. (2 pgs.), Dec. 12, 1990.
Snail, "Reflectometer Design Using Nonimaging Optics", (draft; copy in file history of U.S. Patent No. 4,815,858 to Snail, Issued Mar. 23, 1989).
Brandenberg, "Focusing Properties of Hemispherical and Ellipsoidal Mirror Reflectometers", J. Opt. Sci. Am., vol. 54, No. 10, (Oct. 1964) (incomplete copy).
Jacquez et al, "An Integrating Sphere for Measuring Diffuse Reflectance in the Near Infrared", J. Opt. Sci. Am. vol. 45, No. 10, (Oct. 1955), pp. 781–785.
Gindele et al., "Spectral Reflectance Measurements Using an Integrating Sphere in the Infrared", Applied Optics, vol. 24, No. 12, (Jun., 1985), pp. 1757–1760.
Edwards et al., "Integrating Sphere for Imperfectly Diffuse Samples", Applied Optics, vol. 51, (Nov. 1961), pp. 1279–1288.

(List continued on next page.)

*Primary Examiner*—Hoa Q. Pham
(74) *Attorney, Agent, or Firm*—Sughrue Mion, PLLC

(57) ABSTRACT

Illuminator apparatus for illuminating a workpiece during visual testing thereof, the illuminator comprising: a source of illumination that illuminates a portion of the workpiece with on-axis illumination centered at a first angular direction and having a first intensity and with off-axis illumination having a second intensity; and an optical viewing system, that views said portion of the workpiece and accepts light reflected from the workpiece over a range of angular directions, centered at a second angular direction, said range of angular directions defining said on-axis illumination, wherein said first intensity and second intensity art separately adjustable and wherein the first angular direction is different from the second angular direction.

26 Claims, 6 Drawing Sheets

U.S. PATENT DOCUMENTS

| | | | |
|---|---|---|---|
| 3,229,564 A | 1/1966 | Meltzer | 88/14 |
| 3,251,984 A | 5/1966 | Colterjohn | 240/1.3 |
| 3,270,194 A | 8/1966 | Lee | 240/20 |
| 3,277,773 A | 10/1966 | White | 88/14 |
| 3,365,720 A | 1/1968 | Kelleher | 343/837 |
| 3,375,361 A | 3/1968 | Thompson et al. | 240/1.3 |
| 3,375,752 A | 4/1968 | Fairbanks et al. | 88/24 |
| 3,428,397 A | 2/1969 | Elmer | 355/11 |
| 3,498,714 A | 3/1970 | Elmer | 355/70 |
| 3,560,729 A | 2/1971 | Liberman | 240/9 |
| 3,663,083 A | 5/1972 | Friedman et al. | 350/96 R |
| 3,763,348 A | 10/1973 | Costello | 219/347 |
| 3,806,256 A | 4/1974 | Ishak | 356/186 |
| 3,825,322 A | 7/1974 | Mast | 350/236 |
| 3,920,311 A | 11/1975 | Tsuda et al. | 350/89 |
| 3,923,381 A | 12/1975 | Winston | 350/293 |
| 3,957,031 A | 5/1976 | Winston | 126/270 |
| 4,002,499 A | 1/1977 | Winston | 136/206 |
| 4,003,638 A | 1/1977 | Winston | 350/293 |
| 4,006,355 A | 2/1977 | Shemitz et al. | 240/51.11 |
| 4,027,151 A | 5/1977 | Barthel | 240/41.35 R |
| 4,045,246 A | 8/1977 | Mlavsky et al. | 136/89 PC |
| 4,056,309 A | 11/1977 | Harbison et al. | |
| 4,095,905 A | 6/1978 | Kuni et al. | 356/200 |
| 4,220,982 A | 9/1980 | Martino | 362/97 |
| 4,223,346 A | 9/1980 | Neiheisel et al. | 358/106 |
| 4,287,554 A | 9/1981 | Wolff | 362/218 |
| 4,319,847 A | 3/1982 | Howarth | 356/431 |
| 4,320,442 A | 3/1982 | McCamy | 362/301 |
| 4,360,275 A | 11/1982 | Louderback | 356/446 |
| 4,421,410 A | 12/1983 | Karasaki | |
| 4,423,470 A | 12/1983 | Naito et al. | 362/17 |
| 4,441,817 A | 4/1984 | Pryor | 356/375 |
| 4,449,818 A | 5/1984 | Yamaguchi et al. | |
| 4,460,942 A | 7/1984 | Pizzuti et al. | 362/217 |
| 4,464,050 A | 8/1984 | Kato et al. | 356/237 |
| 4,498,742 A | 2/1985 | Uehara | 350/523 |
| 4,500,202 A | 2/1985 | Smyth | 356/237 |
| 4,506,152 A | 3/1985 | Gupta | 250/216 |
| 4,531,180 A | 7/1985 | Hernandez | 362/297 |
| 4,555,727 A | 11/1985 | Nun et al. | 358/106 |
| 4,597,665 A | 7/1986 | Galbraith et al. | 356/237 |
| 4,661,706 A | 4/1987 | Messerschmidt et al. | 250/341 |
| 4,692,690 A | 9/1987 | Hara et al. | 324/73 PC |
| 4,693,601 A | 9/1987 | Dabelstein et al. | 356/237 |
| 4,710,638 A | 12/1987 | Wood | 250/492.1 |
| 4,714,327 A | 12/1987 | Marshall | 350/504 |
| 4,718,767 A | 1/1988 | Hazama | 356/381 |
| 4,730,895 A | 3/1988 | Siedband et al. | 350/96.24 |
| 4,735,497 A | 4/1988 | Elterman | |
| 4,795,911 A | 1/1989 | Kohno et al. | 250/572 |
| 4,801,810 A | 1/1989 | Koso | |
| 4,815,858 A | 3/1989 | Snail | 356/446 |
| 4,816,686 A | 3/1989 | Hara et al. | 250/458.1 |
| 4,821,114 A | 4/1989 | Gebhardt | 358/75 |
| 4,824,194 A | 4/1989 | Karasawa | 350/96.1 |
| 4,859,064 A | 8/1989 | Messerschmidt et al. | 356/446 |
| 4,877,326 A | 10/1989 | Chadwick et al. | |
| 4,881,802 A | 11/1989 | Stankewitz | 350/525 |
| 4,900,153 A * | 2/1990 | Weber et al. | 356/430 |
| 4,922,107 A | 5/1990 | Rabl et al. | 250/504 R |
| 4,933,817 A | 6/1990 | Mochizuki et al. | 362/33 |
| 4,938,555 A | 7/1990 | Savage | 350/96.15 |
| 5,058,982 A | 10/1991 | Katzir | |
| 5,151,803 A | 9/1992 | Wakita et al. | |
| 5,153,668 A | 10/1992 | Katzir et al. | |
| 5,495,535 A | 2/1996 | Smilansky et al. | |
| 6,437,312 B1 * | 8/2002 | Adler et al. | 250/216 |

OTHER PUBLICATIONS

Goodman, "Illuminator for Dark Field Microscopy", Aug. 15, 1984, Applied Physics, vol. 23, No. 16, pp. 2670–2671.

Goodman, "Illuminators Based on Fiber Rings", Jun. 1, 1985, Applied Physics, vol. 24, No. 11, pp. 1560–1562.

Akio, Y.; JP 56–072431 A; Jun. 16, 1981 and Patent Abstracts of Japan; vol. 005; No. 134 (P–077); Aug. 26, 1981.

Mitsuyoshi, K.; JP 57–019647 A; Feb. 1, 1982 and Patent Abstracts of Japan; vol. 006; No. 082 (P–116); May 20, 1982.

Satoshi, F.; JP 61–029712 A; Feb. 10, 1986 and Patent Abstracts of Japan; vol. 010; No. 183 (P–472); Jun. 26, 1986.

* cited by examiner

ILLUMINATOR FOR INSPECTING SUBSTANTIALLY FLAT SURFACES

FIELD OF THE INVENTION

The invention relates to the illumination of substantially flat surfaces in order to perform visual inspection of the surfaces and in particular to the illumination of printed circuit boards in order to perform visual inspection thereof by machine.

BACKGROUND OF THE INVENTION

Modern printed circuit boards are typically laminated from numerous layers, the planar surface of each layer comprising an intricate pattern of conducting regions, formed for example from 1–2 mil thick copper, separated by regions of non-conducting substrate. A fault in any intermediate layer of the board may result in malfunction of the entire board. Consequently, it has become standard practice to check for the existence, integrity and shape of features existing on each of the printed circuit board layers during manufacturing and prior to lamination.

The inspection of complicated printed circuit board layers is generally done optically by machine. The printed circuit board is placed on the machine to enable partial viewing of the board by the collecting optics of an imaging system, and is subsequently scanned. While passing through the field of view of the collecting optics, it is illuminated by an appropriate illumination system.

In prior art systems a single CCD array and illuminator is typically employed. Such conventional arrays and illuminators are typically insufficiently long to acquire an image of the entire width of the printed circuit board in a single pass. As a result, in addition to moving the board and collecting optics relative to each other in a principal scanning direction, the machine must additionally move the board and collecting optics in a second, orthogonal, direction in order to construct an image of the entire board. The result is a composite, image comprised of long thin contiguous strips, on the order of 0.5 mil wide, acquired sequentially from subsequent passes of the CCD array over different sections of the printed circuit board surface. Each strip approximates the field of view of the CCD array.

The acquired image is next analyzed and a map of features on the board is prepared. This resulting map can then be compared, by computer, to a stored map of predetermined features or design rules to which the board is supposed to conform.

Different regions on a printed circuit board may be distinguished by their reflective behavior when exposed to a source of light. For example, the conducting material on a printed circuit board is generally a more specular, if somewhat diffusing reflector of white light relative to the substrate material which is generally more diffuse. Moreover, by relying on differences in spectral reflection properties, it is possible to enhance the contrast between laminate and conductor by using appropriate color filters.

Because image processing of a an image acquired from a printed circuit board relies on an analysis of the reflective properties of its various features, the process can be highly sensitive to the qualities of the light used to illuminate the board. For example, boards are made up of various materials each having differing reflective properties. Additionally, the surface of boards have a topographical relief that may be resultant both from the cross sectional shape of the conductors, as well a surface microstructure. As a result, the intensity or brightness of a reflection of an inspected feature on a board may be dependent not only on the inherent reflective properties of its materials, but also on its surface topography.

To provide an effective illumination in automated optical inspection applications it is necessary to mitigate the effects of topographical variations on a board's surface. Thus, it is known to highly concentrate light along a relatively thin line by using a source configured to emanate light over a relatively wide solid angle of illumination.

It is believed that the following patents represent the state of the art in high intensity concentrated illumination for automated inspection of printed circuit boards: U.S. Pat. No. 4,421,410 to Karasaki et al, U.S. Pat. No. 4,877,326 to Chadwick et al, U.S. Pat. No. 4,801,810 to Koso, U.S. Pat. No. 5,058,982 to Katzir et al, and U.S. Pat. No. 5,153,668 to Katzir et al., the disclosures of all of which are incorporated herein by reference.

In some conventional illuminators that provide a wide solid angle concentrated illumination, the strip of the board being inspected is illuminated with light from three linear illumination sources that are fixed substantially parallel to the strip. Light from a first of the illumination sources is concentrated onto the strip from a direction substantially perpendicular to the surface of the board by a cylindrical lens or a section of an elliptical cylindrical mirror running the length of the first light source. Light from a second illumination source is concentrated by a similar lens or mirror onto the strip from a first oblique angle with respect to the normal to the surface. Light from a third illumination source is concentrated similarly onto the strip from a second oblique angle to the normal that is equal and opposite to the first oblique angle. In some of the prior art illuminators, the three illumination sources are configured to create a contiguous solid angle of concentrated light.

For the purposes of clarifying terminology as used herein, it is noted that on-axis illumination is defined as illumination that a reflecting surface parallel to the plane of the workpiece would specularly reflect in a direction along the axis of the collecting optics. Off-axis illumination is defined as illumination that is reflected into the collecting optics by surfaces that are not parallel to the plane of the printed circuit board. In the conventional illuminators, the on-axis illumination illuminates the board from a direction substantially normal to the area of the board being illuminated, while the off-axis illuminators each respectively illuminate the board from directions on either side of the on-axis illumination.

The prior art concentrating broad solid angle illuminators comprise many optical components that must be accurately positioned in order to provide a wide solid contiguous angle of illumination. Settings of the various light sources must also be accurately adjusted. Furthermore these settings and positions must be stabilized and accurately maintained in an environment subject to vibration and large heat transfers. Additionally the "seams" or boundaries between the on-axis illumination and the two off-axis illumination regions are generally defined by the edges of the mirrors or lenses used to concentrate on-axis and off-axis illumination on a board. These seams or boundaries are therefore sharp and generally obtrusive. This makes it difficult to assure that on-axis illumination and off-axis illumination are smoothly blended to provide a substantially uniform illumination throughout the broad angle of illumination over the area of an illuminated strip.

As a result of these difficulties, mechanical and optical components of prior art concentrated illuminators require very tight tolerances and are relatively expensive. Furthermore these difficulties have restricted the lengths of the effective region of illumination to the order of 15 cm, which length is often less than the width of the board being inspected.

An illuminator for providing concentrated light, but having an altogether different design is shown in U.S. Pat. No. 4,801,810. In this patent an elliptical reflector comprising approximately one-half of an elliptical cylinder is used to illuminate the surface of a printed circuit board. The axis of the ellipse is placed at an oblique angle to the surface of the board, with the surface being placed at one focus of the ellipse and a single source of illumination being placed at the second focus. An imaging system images the illuminated line on the board from an angle equal (but opposite) to the angle at which it is directly illuminated by the source. This system provides uneven off-axis illumination of the line on the board and does not allow for independent adjustment of on-axis and off-axis illumination since only a single source is used for illuminating the board from all directions.

SUMMARY OF THE INVENTION

The present invention is generally described in the context of illumination and inspection of printed circuit boards or their constituent layers which comprise a metal pattern on a non-conducting substrate. However, as will become evident, the present invention is applicable to the automated inspection of many other types of patterned surfaces such as artwork, negative or positive masters (photomasks), hybrid circuits (with suitable scaling) and the like. To emphasize this broader applicability of the invention, the term "workpiece" is used herein to refer to these broader applications and the term "printed circuit board" is used when referring to printed circuit boards, proper or their constituent layers.

One aspect of some preferred embodiments of the invention provides on-axis and off-axis illumination of workpieces from the same apparently contiguous source, wherein the illumination intensity of the on-axis and off-axis illumination is separately adjustable.

Differently stated, this aspect of the invention provides for a seamless wide angle source of concentrated on-axis and off-axis illumination, wherein the intensity of the illumination for each of the on-axis and off-axis illumination is separately adjustable.

Prior art systems provide for either such adjustability or for a seamless illumination. As indicated above, such seamless illumination is desirable to avoid artifacts in images of printed circuit boards. Separate variation of on-axis and off-axis illumination is desirable to allow for adjustment of the two separate illuminations to achieve a uniform level of lighting, or to account for various reflectivities and roughness of the objects being imaged. For example, when viewing photomasks, in which black lines are formed on a clear substrate and the substrate is imaged against a matte surface, optimal contrast is achieved when the on-axis illumination is zero to avoid specular reflection from the "black" lines which reflect weakly, but specularly. Additionally, the signal to noise ratio of images of printed circuit boards may be optimized by reducing the intensity of off-axis illumination relative to the on-axis illumination. This is the result of an increase in reflection from the non-conducting portions of the boards and a decrease in mottling as off-axis illumination is increased.

An aspect of some preferred embodiments of the present invention provides for the center of the on-axis illumination to be at an oblique angle to the surface of the workpiece. In addition, the angular extent of the off-axis illumination is preferably substantially equal on both sides of the on-axis illumination.

Another aspect of some preferred embodiments of the present invention also provides for the center of the on-axis illumination to be at an oblique angle to the surface of the workpiece. In addition, this aspect provides for the on-axis and off-axis illumination to be separately adjustable.

As known to the inventors, prior art systems which provide for the center of the on-axis illumination to be at an oblique angle to the surface of printed circuit boards provide for neither separate adjustability nor equal angular extent of the off-axis illumination on either side of the on-axis illumination.

Equal angular extent of off-axis illumination results in less mottle, while oblique illumination allows for a seamless transition between the on-axis and the off-axis illumination. However, the combination of these qualities in a single illumination system has not been available in the prior art.

Furthermore, prior art systems with non-normal on-axis illumination provided illumination from substantially all directions above the surface being illuminated (except for the direction of the imaging system). The present inventors have determined that it is desirable to limit the extent of off-axis illumination, at least when viewing printed circuit boards, since, while the mottle is decreased with increasing angle of illumination, the signal from the nonmetallic portions of the workpiece increases faster than that from the metallic portion, resulting in a reduction in signal to noise ratio.

One aspect of some preferred embodiments of the present invention provides an illuminator for providing a wide solid angle of continuous concentrated illumination, comprising fewer optical elements than many prior art broad angle concentrating illuminators and/or less complicated construction of the parts.

Another aspect of some preferred embodiments of the present invention provides for a smooth seamless off-axis illumination and seamless blending of on-axis and off-axis illumination in an illuminator providing wide solid angle of continuous illumination, even when the intensities of the on-axis and off-axis sources are different.

Another aspect of some preferred embodiments of the present invention provides an illuminator that can provide wide solid angle of concentrated illumination for strips on the surface of a workpiece that are longer than strips that are illuminated by prior wide solid angle concentrating illuminators. This is made possible, in some measure, by the simplification in construction of the parts used in the system and in their alignment.

According to another aspect of some preferred embodiments of the present invention, a method is provided for determining the position and size of an optimum virtual illumination source to be used as a source of illumination when the actual source of illumination is used with a diffuser.

According to still another aspect of some preferred embodiments of the present invention an automated optical inspection system is provided, wherein inspected workpieces are illuminated using an illuminator configured according to the teachings herein.

According to still another aspect of some preferred embodiments of the present invention, a method for inspecting workpieces is provided, such method incorporating the steps of illuminating the workpiece with illumination provided by an illuminator according to the teachings herein.

According to an additional aspect of some preferred embodiments, a suitable reflector for use in the illuminator according to the teachings herein, and method for manufacture thereof, is provided.

An illuminator in accordance with a preferred embodiment of the present invention comprises a single linear light source hereafter referred to as an "on-axis source" to provide on-axis illumination. A different single linear light source, hereafter referred to as an "off-axis source", provides off-axis illumination.

In a preferred embodiment of the invention, a first, off-axis, illumination source is placed substantially at one focus of a reflector which forms a minor part of a cylindrical elliptical surface. The workpiece is placed at the other focus of the reflector. The workpiece is oriented at an angle to the off-axis illumination such that, if the workpiece were a specular reflector, light reflected from it would be oriented such that it would not be reflected back toward the mirror. Thus, the surface of the workpiece is not perpendicular to the center of the off-axis illumination.

In a preferred embodiment of the invention, a narrow rectangular planar strip mirror is placed between the off-axis source and the reflector, such that the off-axis illumination reaching the workpiece is split into two non-joining parts, each part having a substantially equal angle of illumination and separated by an angular wedge shaped gap. Image collecting optics is placed such that its axis just intercepts the extreme edge of the off-axis illumination.

In a preferred embodiment of the invention, the on-axis source is placed substantially at a virtual focus of the ellipse as reflected by the planar strip mirror. Light from this source will be reflected from the mirror and will illuminate the workpiece with on-axis illumination with respect to the collecting optics. The two sources will provide a seamless illumination of the workpiece since light from the off-axis source will illuminate from angles which are not "covered" by the strip and the on-axis source will illuminate only from central angles thus filling the gap between the parts of the off-axis illumination. This system is seamless, self aligning and provides for off-axis and on-axis illumination, seemingly from a single source but which has separate adjustability for the off-axis and on-axis illumination respectively.

In a preferred embodiment of the invention, a diffuser is placed in front of each of the off-axis and on-axis sources such that each of these sources provides a different, broader effective source of illumination. One aspect of some embodiments of the invention provides a method of determining the effective width and effective position of the resulting sources of illumination.

Yet another aspect of some preferred embodiments of the invention provides for multi-spectral detection of light reflected from the workpiece. In a preferred embodiment of the invention, R, G & B are separately detected and a composite "gray level" reflection value is generated by weighting the measured intensities of the three detected colors. Preferably the weighting is determined to give an optimum contrast between the metal and substrate for printed circuit boards (or for other workpieces in which the elements being differentiated have different colors) and is a function of color of the two materials, of the color of the illumination and possibly of the extent of the illumination. It should be understood that other methods of weighting such as filtering of the reflected light may be utilized. However, such methods are less precise and generally less efficient than weighting the signals. In a preferred embodiment of the invention, the light is preconditioned, as by filtering, to provide substantially independent detection of different spectral segments by the detectors.

There is thus provided, in accordance with a preferred embodiment of the invention, illuminator apparatus for illuminating a workpiece during visual testing thereof, the illuminator comprising:

a source of illumination that illuminates a portion of the workpiece with on axis illumination having a first intensity and off-axis illumination having a second intensity; and an optical viewing system, that views said portion of the workpiece and accepts light reflected from the workpiece over a range of angular directions, said range of angular directions defining said on-axis illumination, wherein said on-axis and off-axis illumination have separately adjustable intensities and appear to emanate from a contiguous source.

There is further provided, in accordance with a preferred embodiment of the invention, illuminator apparatus for illuminating a workpiece during visual testing thereof, the illuminator comprising:

a source of illumination that illuminates a portion of the workpiece with on-axis illumination centered at a first angular direction and having a first intensity and with off-axis illumination having a second intensity; and an optical viewing system, that views said portion of the workpiece and accepts light reflected from the workpiece over a range of angular directions, centered at a second angular direction, said range of angular directions defining said on-axis illumination, wherein said first intensity and second intensity are separately adjustable and wherein the first angular direction is different from the second angular direction.

Preferably, the off-axis and on-axis illumination together illuminate the workpiece over a second range of angles, said second range of angles being substantially centered at said first angular direction.

Preferably, the illumination illuminates the workpiece from angles ranging over substantially less than a total range of 180°, more preferably less than 100°.

In accordance with a preferred embodiment of the invention, the source of illumination includes a first source of illumination that produces the on-axis illumination and a second source of illumination that produces the off-axis illumination. Preferably, the illumination produced by the first source and the second source illuminate the workpiece without any gap between the on-axis and off-axis illumination. Preferably, the apparatus includes a mirror from which the first source is reflected to illuminate the workpiece. Preferably, the mirror has an extent and the second source is situated behind the mirror such that the mirror blocks illumination therefrom from illuminating the workpiece and wherein said off-axis illumination is comprised of illumination from the second source which passes the mirror outside its extent. Preferably, the mirror is mounted on a transparent substrate having an extent greater than the extent of the mirror.

In a preferred embodiment of the invention, the first source and the second source are substantially optically equidistant from the mirror.

A preferred embodiment of the invention includes a concentrating mirror that receives illumination from the first and second sources and concentrates the illumination onto the workpiece. Preferably, the concentrating mirror comprises an elliptical mirror portion. Preferably, the first and second sources are optically situated substantially at a focus of the elliptical mirror.

In a preferred embodiment of the invention, the concentrating mirror comprises a base having the general shape of the mirror and a metal foil adhered to the base. Preferably, the metal foil is adhered to the base by a vacuum applied to the metal foil.

In a preferred embodiment of the invention, the workpiece is situated substantially at a second focus of the elliptical mirror.

In a preferred embodiment of the invention the first source and the second source are line sources. Preferably, the line source comprises a radiant line source and a diffuser through which light that illuminates the workpiece from said line source passes.

There is further provided, in accordance with a preferred embodiment of the invention, apparatus for visual inspection of a workpiece comprising:

illumination apparatus according to any of the preceding claims; and
  an optical sensor that receives light from the optical viewing system and produces image signals in response thereto.

Preferably, the apparatus includes:

means for moving the workpiece relative to the illumination apparatus such that the optical sensor produces image signals representative of successive portions of the workpiece.

Preferably, the on-axis illumination illuminates the workpiece from a range of directions having an angular extent of between about 4° and about 8°, more preferably about 6°.

In a preferred embodiment of the invention, the on-axis and off-axis illumination illuminate the workpiece from a range of directions having an angular extent of between 30° and about 60°, more preferably between about 39° and 45°.

In preferred embodiments of the invention, the workpiece comprises a printed circuit board.

There is further provided, in accordance with a preferred embodiment of the invention, a mirror comprising:

a base having the general shape of the mirror; and
  a metal foil forming a mirror surface adhered to the base by a vacuum.

Preferably, the metal foil has a thickness between about 0.25 mm and about 0.45 mm, more preferably between about 0.25 mm and about 0.35 mm and most preferably about 0.35 mm.

There is further provided, in accordance with a preferred embodiment of the invention, an illuminating system for illuminating a workpiece during visual inspection thereof, comprising:

a linear source of radiation, comprising:
    a line source;
    a diffuser: situated on one side of the line source; and
  a reflector having at least one focus situated on the other side of the diffuser from the line source, wherein an effective position of the linear source of radiation situated between the line source and the diffuser is situated at the focus of the reflector.

There is further provided, in accordance with a preferred embodiment of the invention, an illuminating system for illuminating a workpiece during visual inspection thereof, comprising:

a light source emitting light over a continuous angle of illumination toward the workpiece;
  a blocking element that block light over a portion of the continuous angle such that two portions of the illumination, separated by a blocked angle illuminate the workpiece from the source.

Preferably the apparatus comprises a concentrator that receives the unblocked portions of light and concentrates the illumination onto the workpiece. Preferably, the source of light is placed at a focus of the concentrator. Preferably, light from the source of light is concentrated at a focus of the concentrator. Preferably, the concentrator is a mirror.

In a preferred embodiment of the invention the concentrator is an elliptical mirror and wherein the source of light is situated at one focus of the elliptical mirror and the light emitted by the source is concentrated at a second focus of the elliptical mirror.

Preferably, the position of the blocking element is adjustable, such that the angular extent of the two sections of illumination is adjustable.

Preferably, the blocking element supplies illumination to the workpiece over the blocked portion of the continuous angle.

In a preferred embodiment of the invention, the blocking element comprises a planar strip mirror having a mirrored surface facing away from the light source. Preferably, the apparatus includes an additional source of illumination that supplies illumination to the mirror from which it is reflected in generally the same direction as the illumination from the light source. Preferably, the light source are at the same effective position when viewed from the mirror side of the strip mirror.

In a preferred embodiment of the invention one or more of the intensity, polarization and wavelength of at least one of the light source and the additional source are separately adjustable.

There is further provided, in accordance with a preferred embodiment of the invention, an automated optical inspection system for inspecting substantially flat workpieces, comprising:

illuminating apparatus as described above;
  an imager that images a workpiece illuminated by the illuminator; and
  an image analyzer that analyzes the image and determines the existence of defects in the workpiece.

The invention will be more clearly understood by reference to the following description of preferred embodiments thereof read in conjunction with the accompanying figures. Identical structures, elements or parts that appear in more than one of the figures are labeled with the same numeral in all the figures in which they appear. Analogous structures, elements or parts that appear in more that one of the figures are labeled with an analogous series of numerals in the figures in which they appear.

DETAILED DESCRIPTION OF PREFERRED EMBODIMENTS

Figure 1:
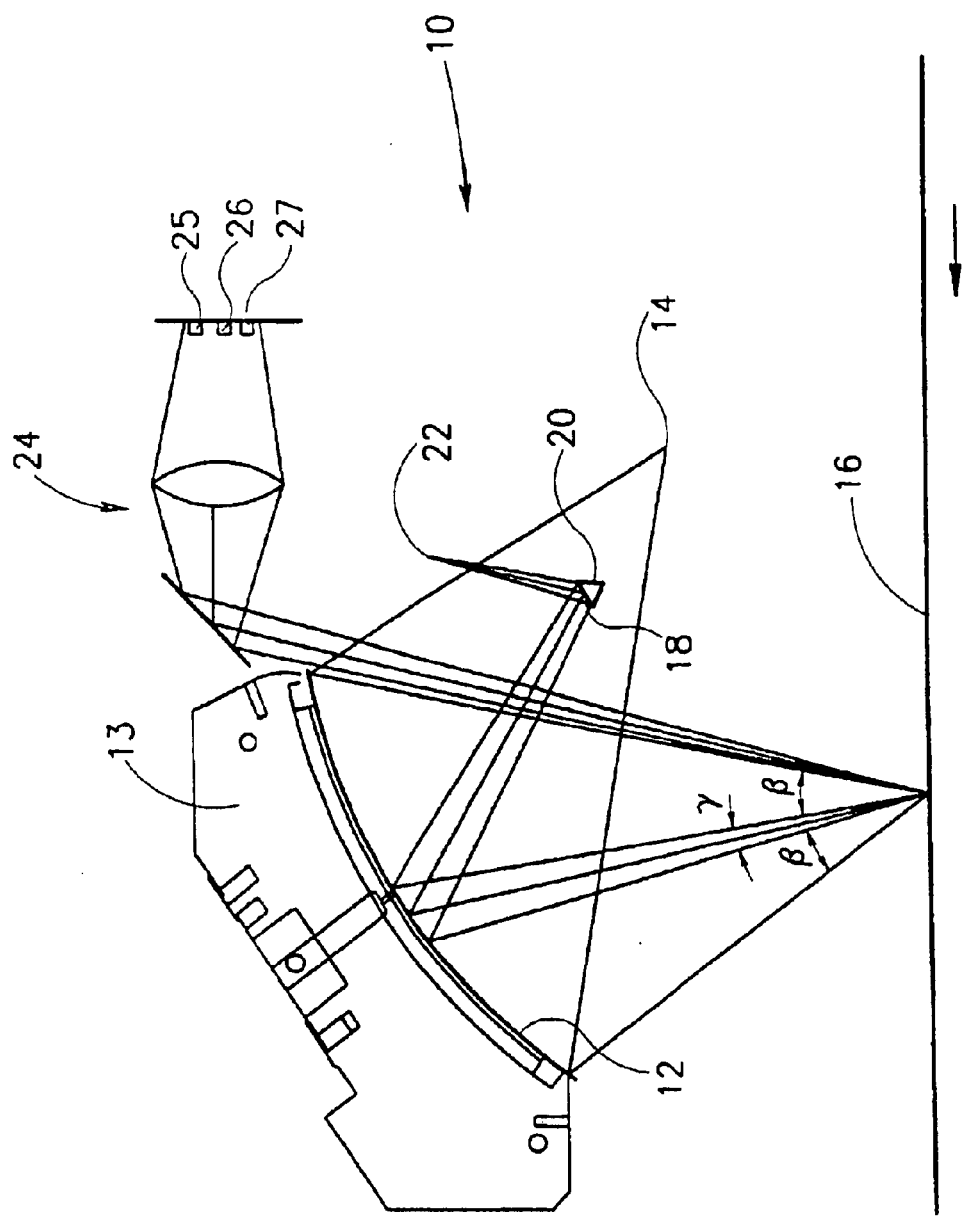
FIG. 1 shows a simplified cross sectional view of an illuminator, in accordance with a preferred embodiment of the invention.
Figure 2:
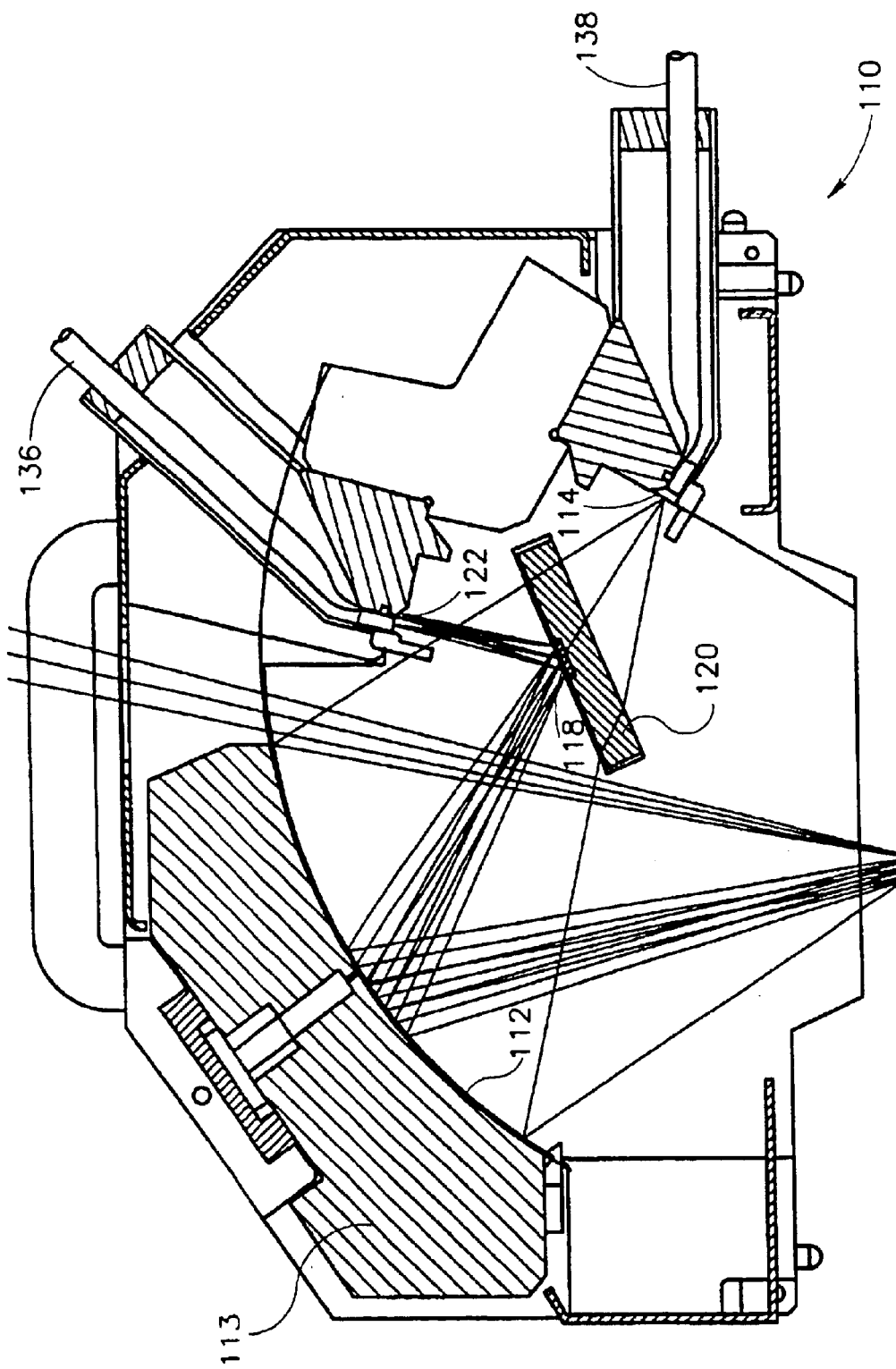
FIG. 2 is a schematic cross-sectional view of an illuminator, in accordance with a preferred embodiment of the invention.

FIG. 1 shows a perspective view of a simplified schematic of an illuminator 10, in accordance with a preferred embodiment of the present invention. Illuminator 10 comprises a cylindrical reflector or mirror 12 having a substantially elliptical shape and a limited extent with an off-axis substantially uniform linear source of illumination 14 placed at one focus thereof and a workpiece or other substrate 16, to be optically examined placed at another focus thereof. A front surface strip mirror 18 is placed between off-axis source 14 and mirror 12, with the mirrored surface facing away from off-axis source 14. The width of strip mirror 18 is such that it allows light from off-axis source 14 to be concentrated by mirror 12 and to reach substrate 16 from two angular sectors each having a width β each as shown, separated by a wedge shaped region of angular extent γ. It should be noted that while strip mirror 18 is shown as being mounted on a substrate 20 which has the same width as strip mirror 18, substrate 20 may be wider than the strip mirror it supports (as shown in FIG. 2). It is readily appreciated that the position and arrangement of mirror 12 may be adjusted to adjust the relative angular extents of each of sectors β.

A narrow substrate 20, as shown, may be formed completely of metal. Such a structure introduces fewer aberrations into the off-axis illumination than when a wide glass support is used. The choice between the two structures is based, at least in part by the length of the strip mirror and the stability requirements of the system. In a preferred embodiment of the invention, the dimension (β+γ/2) may vary from about 15° to 30°, and most preferably is about 19.5° to 22.5°. In a preferred embodiment of the invention γ may vary from about 4° to 8° and most preferably is about 6°.

A second, on-axis linear illumination source 22, similar to off-axis source 14, is placed, in accordance with a preferred embodiment of the invention, substantially at the reflection of the focus of the elliptical reflector as reflected by strip mirror 18. Thus, illumination from on-axis source 22, reflected by strip mirror 18 illuminates the other focus of the elliptical reflector within the same angular extent as that which mirror 18 blocks the illumination from source 14, namely the angle γ.

To more clearly understand how a preferred embodiment of the illumination system of FIG. 1 provides substantially seamless illumination, assume that only the off-axis source 14 is on. Light rays from the off-axis source 14 that are incident on the back surface of strip mirror 18 are "shadowed out" from the front side of the strip mirror. Strip mirror blocks these rays and they are thus are not concentrated by mirror 18 onto workpiece 16. Light rays from off-axis source 14 that are not incident on the strip mirror pass to the right and left sides of the strip mirror 18.

Assume the on-axis source 22 is turned on. Light rays from the on-axis source 22, which is adjacent to the front side of strip mirror 18, are incident on the front surface of strip mirror 22, and are reflected therefrom to reflector 12. Light rays from on-axis source 22 that are not incident on the strip mirror pass to the back side of the strip mirror.

Because the on-axis source is at substantially the same point optically as the off-axis source, light rays from the on-axis illumination source that are reflected back to the front side of the strip mirror appear to come from the same point as does the off-axis illumination source. If the angular radiance of the two sources is the same, these reflected light rays from the on-axis source replace those light rays from the off-axis source in the gap shadowed out by the strip mirror. The strip mirror "seamlessly" combines light from the off-axis illumination source and the on-axis illumination source so that all the light on the front side of the strip mirror appears to be radiated by a single illumination source. The alignment of such a system is thus seen to be not only simple and straightforward but also much less critical than that of most prior art systems. Furthermore, the optical components may be less precise than in prior art systems. Finally, the number of components is generally reduced and the components are more simply (and inexpensively) formed and assembled.

In a preferred embodiment of the invention, sources 14 and 22 are provided by illuminating a fiber bundle and then spreading the fibers into a line source. This provides a uniform linear illumination source.

While the angular extent of the left and right off-axis illumination is adjustable by positioning of strip mirror 18, it has been found to preferably be substantially the same. It may be noted that when the angular extent of each of the left and right off-axis illuminations is the same, the portion of mirror 12 which is illuminated by each of the left and right off-axis illuminations is not the same.

It may also be noted that the illumination intensity of the on-axis and off-axis sources respectively may be individually adjusted. This allows for attaining an even illumination across the entire angle of illumination (2β+γ), or for making either the intensity of either the on-axis illumination or the off-axis illumination stronger relative to the other. Alternatively or additionally the polarization or wavelength of the off-axis and/or the on-axis sources may be varied.

In a preferred embodiment of the invention mirror 12 is formed of an aluminum foil having a nominal thickness of preferably between about 0.25 mm and 0.35 mm, most preferably about 0.35 mm±about 5 micron. These values are chosen to give reasonable precision and stability to the mirror. In a preferred embodiment of the invention, mirror 12 is mounted on a machined part 13 to which it is attached by vacuum (with a reflective surface facing away from the machined part) such that the required optical surface finish is provided by the aluminum foil and the shape is provided by the machined part.

Collecting optics 24 is provided to image the illuminated line on the workpiece onto a plurality of detectors, (such as CCD elements) preferably formed into one or more line detectors 25, 26 and 27 (shown as points on FIG. 1 since they are viewed end on). The axis of collector optics 24 is oriented at an angle with respect to the workpiece such that it would intercept the central ray of the on-axis illumination that would be reflected from the workpiece, were the workpiece to be a specular reflector. The aperture of the collector optics is such that it would be overfilled by the on-axis radiation from such a specular surface. In a preferred embodiment of the invention, as will be described in greater detail below, a series of axially spaced lenses or lens systems forming an optical array 28 (FIG. 6) is provided, each of which lens systems images one of a plurality of preferably overlapping portions of the illuminated portion of the workpiece onto CCD lines 25–27.

Each of the CCD line detectors may comprise a single axial line of such detector elements or a strip a few elements wide. Such a strip preferably images a strip segment of the workpiece which is about 0.5 min wide. This width and the spacing of the CCD elements in a line detector may vary depending on the desired measurement resolution of the system. It should be understood that the effective optical length and spacing of the CCD elements in the direction of motion of the workpiece depends on the sampling rate of the signal from the detectors and the velocity of the workpiece as it passed through the illuminator.

In a preferred embodiment of the invention, multi-spectral detection of light reflected from the workpiece is performed, and each of lines 25–27 is sensitive to a different, preferably substantially non-overlapping, portion of the spectrum. In a preferred embodiment of the invention, R G & B are separately detected and a composite "gray level" reflection value is generated by weighting the measured intensities of the three detected colors. Preferably the weighting is determined to give an optimum contrast between the metal and bare substrate, and is a function of color of the two materials, of the color of the illumination and possibly of the extent of the illumination. It should be understood that other methods of weighting such as filtering of the reflected light by filters (not shown) may be utilized. However, such methods are less precise and generally less efficient than weighting the signals. In a preferred embodiment of the invention, the light is preconditioned, as by filtering, to provide substantially independent detection of different spectral segments by the detectors. This may be desirable when the detector elements are sensitive to overlapping spectral segments.

In preferred embodiments of the invention, one or more improvements and/or variants on the basic system as described with respect to FIG. 1 may be employed. These improvements are described together with respect to FIGS. 2 and 3. However, it should be understood that preferred embodiments of the invention may have one or more, or none of the embellishments of FIGS. 2 and 3.

In accordance with a preferred embodiment of the invention, each of linear sources 14 and 22 (FIG. 1) comprises, now as shown in illuminator 110 (FIG. 2) a wide strip of source illumination, 114 and 122. For simplicity of the drawing, only on-axis source 122 in FIG. 2 is shown as an extended source. As is evident from FIG. 2, on-axis-source 122 illuminates a region of a workpiece 116 having a given width rather than the line illumination shown in FIG. 1.

In general, the illumination system shown has aberrations. Since the acceptance angle of the off-axis illumination is larger than that of the on-axis illumination and since it depends on a larger portion of mirror 112 for its focusing effect, it can be expected to be more subject to variations in intensity near the edges of the field. Therefore, in a preferred embodiment of the invention, source 114 is wider than source 122. Preferably, only that portion of the workpiece for which uniform illumination by source 122 is provided, is used in the analysis of the workpiece.

FIG. 2 also shows the effect of a finite thickness and extent of substrate 120 on which strip mirror 118 is mounted. The net effect of the substrate 120 is to cause a slight deflection in the position of source 114 as well as a difference in aberrations for the on-axis and off-axis illumination. This causes a small but usually unobjectionable, and sometimes desirable, smoothing of the joining of the off-axis and on-axis illumination. Preferably source 114 will be slightly broadened to prevent loss of illuminance uniformity due to the aberrations.

The uniformity of illumination is controlled by the relative radiance of on-axis illumination and off-axis illumination as observed at each point in the strip region being illuminated 123. When the radiance (light flux per unit area and unit solid angle) of light radiated by the on-axis illumination source is controlled to be substantially equal to the radiance of light radiated by the off-axis illumination source, each point in the illuminated strip region 123 is illuminated by substantially equal illumination intensity for incident angles of light rays between angles $\pm(\beta+\beta/2)$. Under these conditions, in the range of incident angles between $\pm(\beta+\gamma/2)$, an illuminator in accordance with a preferred embodiment of the present invention provides substantially uniform illumination. For PCB inspection, the total half angle $\pm(\beta+\gamma/2)$ is preferably limited to less than 30°, and more preferably to about 22.5°, so as to obtain an optimum contrast and signal to noise ratio.

In an illuminator in accordance with a preferred embodiment of the present invention, strip mirror 118 is a narrow reflecting lamination or deposit on a planar surface of a relatively rectangular substrate 120, such as a plate of glass. Strip mirror 118 and off-axis light source 114 are preferably positioned with respect to the substrate 120, and the substrate 120 is preferably sufficiently wide, so that all the light from the off-axis illumination source that is concentrated onto a strip of a workpiece passes through the glass of substrate 120.

Figure 3:
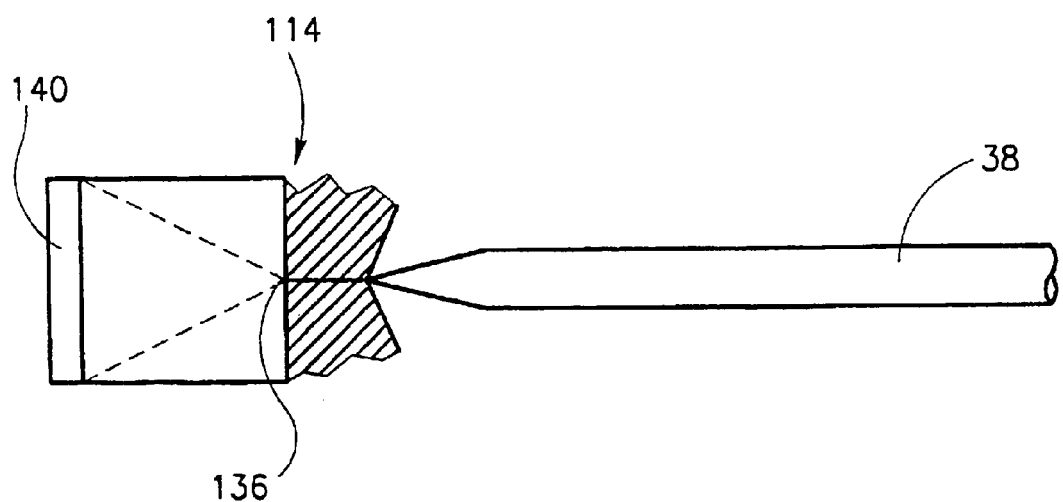
FIG. 3 is a schematic cross section of a diffused source, in accordance with a preferred embodiment of the invention.
Figure 5:
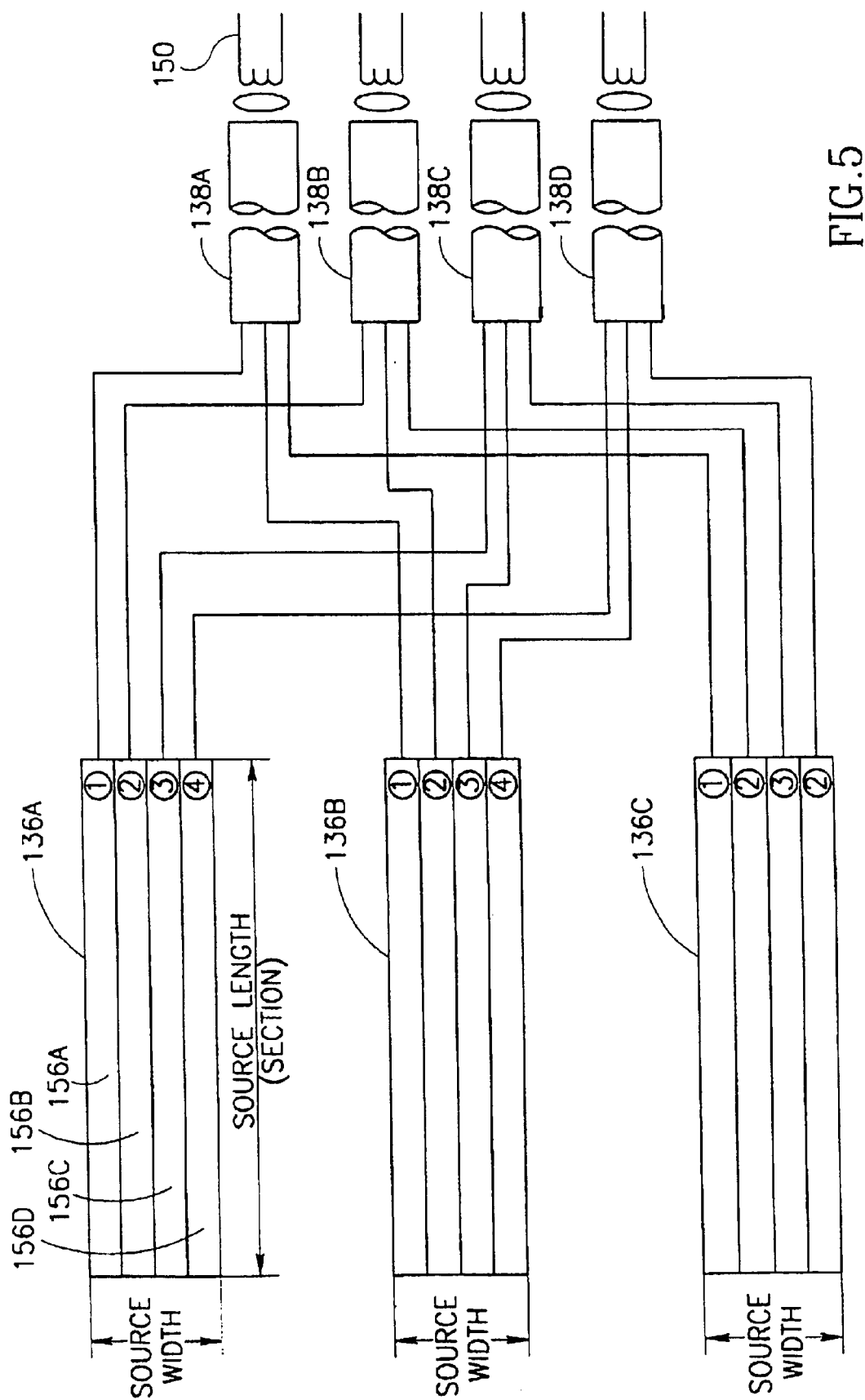
FIG. 5 schematically illustrates a method of illuminating and constructing a long linear source of illumination; in accordance with a preferred embodiment of the invention.

The structure of a preferred illumination source for use with a preferred embodiment of the present invention shown in FIG. 2, is now shown in FIG. 3. Linear light sources 114 and 122 used for on-axis and off-axis illumination preferably comprise ends of optical fibers 136 that are fanned out from at least one fiber bundle 138 so that the ends are coplanar and lie in a dense linear array having a shape of a long narrow rectangle. The bundle of end or ends of the fiber bundle is optically coupled to a lamp or a plurality of lamps 150 (FIG. 5). Light from the lamps is piped through the length of the optical fibers to the ends of the optical fibers in the linear array, from which ends the light is radiated.

FIG. 5 shows, schematically, the construction of light source 114, in accordance with a preferred embodiment of the invention. In accordance with a preferred embodiment of the invention, a very long strip of the workpiece is to be illuminated, preferably of the order of 660 mm. In order to provide such a long strip of illumination and to assure uniform light intensity along the entire strip, a plurality of light sources, such as high intensity lamps 150 (suitably 250 W HLX reflector type quartz halogen lamps provided by Osram Corporation) are utilized. Each of lamps 150 illuminates a bundle 38 of optical fibers. As shown in FIG. 5 four lamps 150 and four bundles 138A–138D are preferably used for off-axis source 114. At one end of bundles 138A–138D the fibers are formed into three sets of fiber ends 136A–136C. Each set 136A–136C comprises four layers 156A–156D, each layer being formed from fibers from one of bundles 138A–138D. Thus, each of sets 136A–136C comprises four layers of light fiber ends each layer being illuminated by a different light source. The total light supplied to each of the sets is equal and this equality does not depend on the balance between the light sources.

In a preferred embodiment of the invention, the four layer sets 136A–136C are laid end to end to form a uniform linear light source four fiber layers thick (about 0.56 mm) and over 660 mm long. This light source has been and will continue to be referred herein to as fiber ends 136.

In an exemplary embodiment of the invention, each fiber bundle includes 17,025 fibers, each having an 80 micrometer diameter. Suitable optical fiber bundles are available from the Schott Company of Germany.

Light source 122 is produced in a manner similar to that employed in the production of source 114, except that only two fiber bundles and associated lamps are employed. Thus each of the three sections 136 is constructed of only two layers (one from each bundle) and the light source is only 0.28 mm thick.

In the preferred embodiment of the light source according to the invention shown in FIG. 3, light radiated from the fiber ends 136 is incident on a diffuser 140 which is parallel to the array of fiber ends 136 and substantially perpendicular to central light rays in a substantially wedge shaped beam of light radiated by the array of fiber ends.

The light incident on the diffuser produces an illuminated band on the diffuser that is defined by a width, and on passing through the diffuser the light appears to emanate from a magnified virtual linear light source behind the diffuser.

Figure 4:
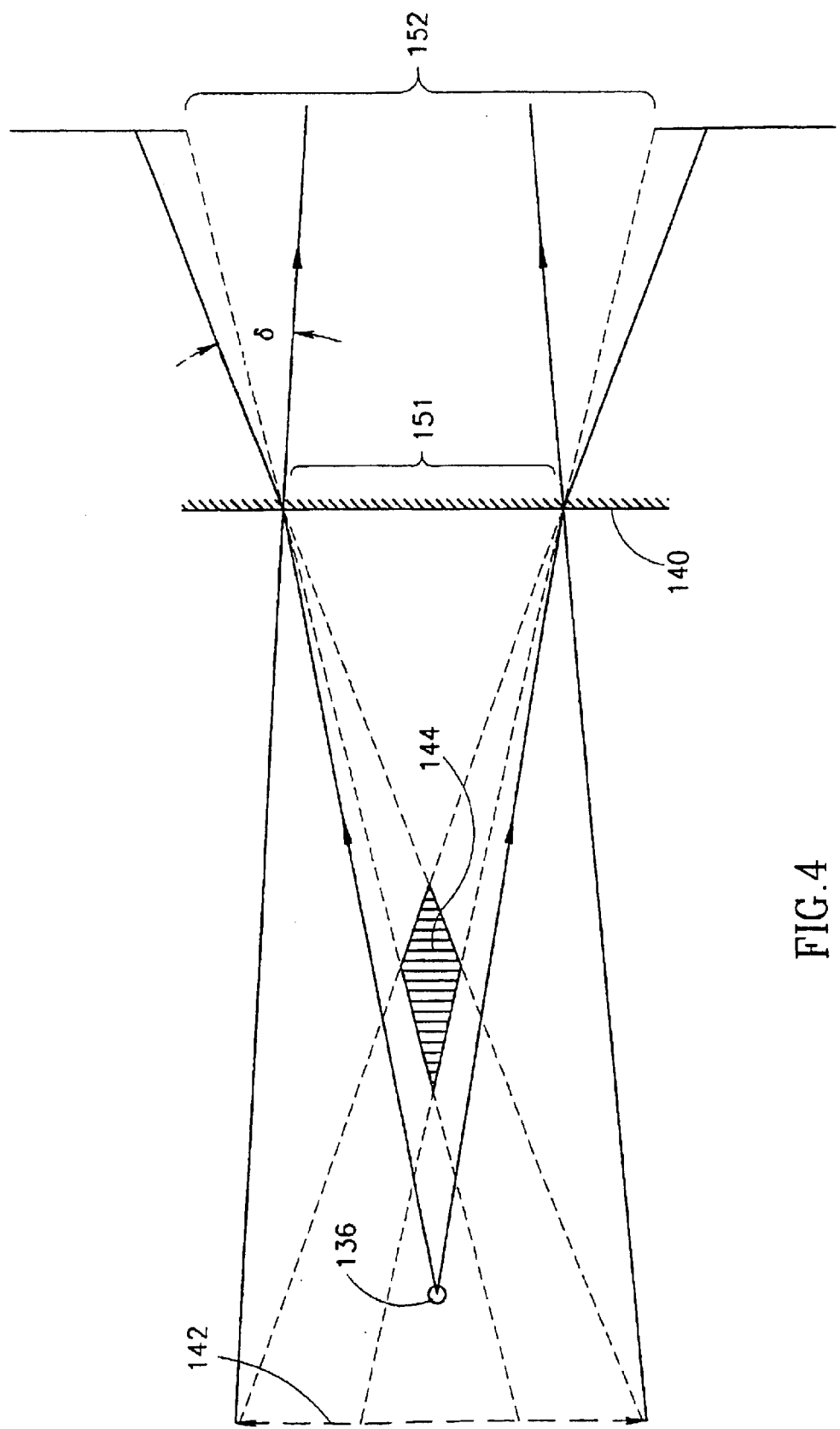
FIG. 4 illustrates ray tracing of light rays used to determine a virtual light source corresponding to the source of FIG. 3, in accordance with a preferred embodiment of the invention.

The present inventors have found, using a ray tracing technique as illustrated in FIG. 4, that, in fact, the apparent source of the illumination is neither diffuser surface 140 nor the fiber ends 136. Rather, the light actually appears to be emanating from a virtual light source 142 located behind actual source. However, the present inventors have surprisingly found that the position and width of an effective light source is different from that of both fiber ends 136 and the virtual source 142. Rather it is defined by a long four sided strip 144 which is referred to herein as a "virtual effective source." This source is situated between the virtual linear light source 142 and the diffuser 140. The size and location of the virtual source is determined mainly by the width 151 of the illuminated band on the diffuser and the aperture 152 of the elliptically cylindrical mirror, for the off-axis source and the strip mirror for the on-axis source. It is also affected by the diffusing angle δ of the diffuser. While the workpiece is actually illuminated by light outside of the virtual light source, this light supplies uneven illumination since it is vignetted because not all of it passes through the aperture of the system.

The virtual effective light source is thus that source which provides substantially unvignetted illumination of the workpiece, and for the purposes of illuminating the workpiece, provides desirable lighting. Preferably, the one focus of reflector 112 is optically coincident with the virtual source 144 (after correction for the effect of substrate 120 for the off-axis source), as a result of which the uniformity of intensity of concentrated illumination of the strip on the workpiece across the width of the strip is improved. Light emerging from regions far from the focus of the reflector and especially from outside the virtual effective source are not in focus at the workpiece surface.

Aberrations in optical elements of an illuminator constructed according to the teachings herein generally distort and blur the image of the effective light source. This effect further limits the region of the workpiece which is uniformly illuminated, i.e. the region that receives light from all parts of the illuminating aperture within the angle ±(β+γ/2). The effect of the aberrations is to partially eclipse parts of the illuminating aperture. Generally, off-axis illumination is more susceptible to distortion than on-axis illumination because larger optical apertures and incidence angles are used to focus off-axis illumination than on-axis illumination. For example, in prior art illuminators two separate optical systems are generally used for off-axis illumination while only one optical system is used to focus on-axis illumination.

In order to accommodate aberrations and compensate for their effects, in accordance with a preferred embodiment of the present invention, the widths of the on- and off-axis sources are different so that strips that are illuminated by on- and off-axis illumination on a workpiece being inspected are wider than would be needed in the absence of aberrations. The required width of each respective source is determined by tracing rays from the required region on the workpiece back to the source plane through all optics, while accounting for production tolerances. The required source width should encompass all such back traced rays. A relatively uniform illuminated strip within the "widened" on- and off-axis strips is located and used for inspection of the workpiece. The positions of the fiber ends 36 and their distance from the diffuser is chosen to provide an effective light source having an extent which provides the desired width of illumination of the surface of the workpiece by the on-axis and off-axis illumination.

As indicated above the off-axis illumination is more susceptible to distortion than the on-axis illumination. In accordance with a preferred embodiment of the present invention, the width of the off-axis illumination source is preferably larger than the width of the on-axis source so that the off-axis illumination illuminates a wider strip on the workpiece than the higher quality on-axis illumination. The area in which the on-axis and off-axis illumination overlaps is scanned to locate an optimum, relatively straight, distortion free illuminated strip appropriately illuminated by on- and off-axis illumination. This optimum illuminated strip (generally narrower than the strip illuminated by the on-axis illumination) is the strip on which the collecting optics of an imaging system used to inspect the workpiece are focused and which is imaged on the detectors.

This scanning is performed in the absence of a workpiece using a microscope which images light radiated by the on- and off-axis illumination sources in the region where both sources are concentrated in order to illuminate a strip on a workpiece. The microscope is controlled to travel the length of the region where the on- and off-axis illumination are concentrated and the position of the microscope is accurately monitored as it moves. Light from the on- and off-axis sources imaged by the microscope is analyzed to determine the size and location of an optimum illuminated strip on which to focus the collecting optics of an imaging system.

From the above discussion it is seen that an illuminator, in accordance with a preferred embodiment of the present invention, comprises a reduced number of optical elements and/or elements which are easier to fabricate and/or are easier to assemble into the illuminator, in comparison to most prior art illuminators. An illuminator, in accordance with a preferred embodiment of the present invention, provides separately adjustable on-axis illumination and substantially symmetric off-axis illumination for all points in an illuminated strip using two light sources and a single focusing system. Prior art illuminators which provide separate adjustment of the on-axis and off-axis illumination generally use at least three light sources, each with its own focusing system. As a result, an illuminator in accordance with a preferred embodiment of the present invention is comparatively simple, and requires machining tolerances for components that are generally not as severe as the tolerances required for components used in prior art illuminators.

An immediate benefit of these advantages is not only the potentially reduced manufacturing costs. An illuminator in accordance with a preferred embodiment of the present invention is capable of providing illumination for strips on a workpiece that are much longer than those that can be effectively illuminated by prior art illuminators. This enables large workpieces that according to prior art required at least two passes through an inspection system to be inspected, completely inspected, in accordance with a preferred embodiment of the present invention, in a single pass through an inspection system. The inventors of the present invention have found that an illuminator in accordance with a preferred, embodiment of the present invention can provide effective illumination for a strip on a workpiece having a length greater than 60 cm.

Figure 6:
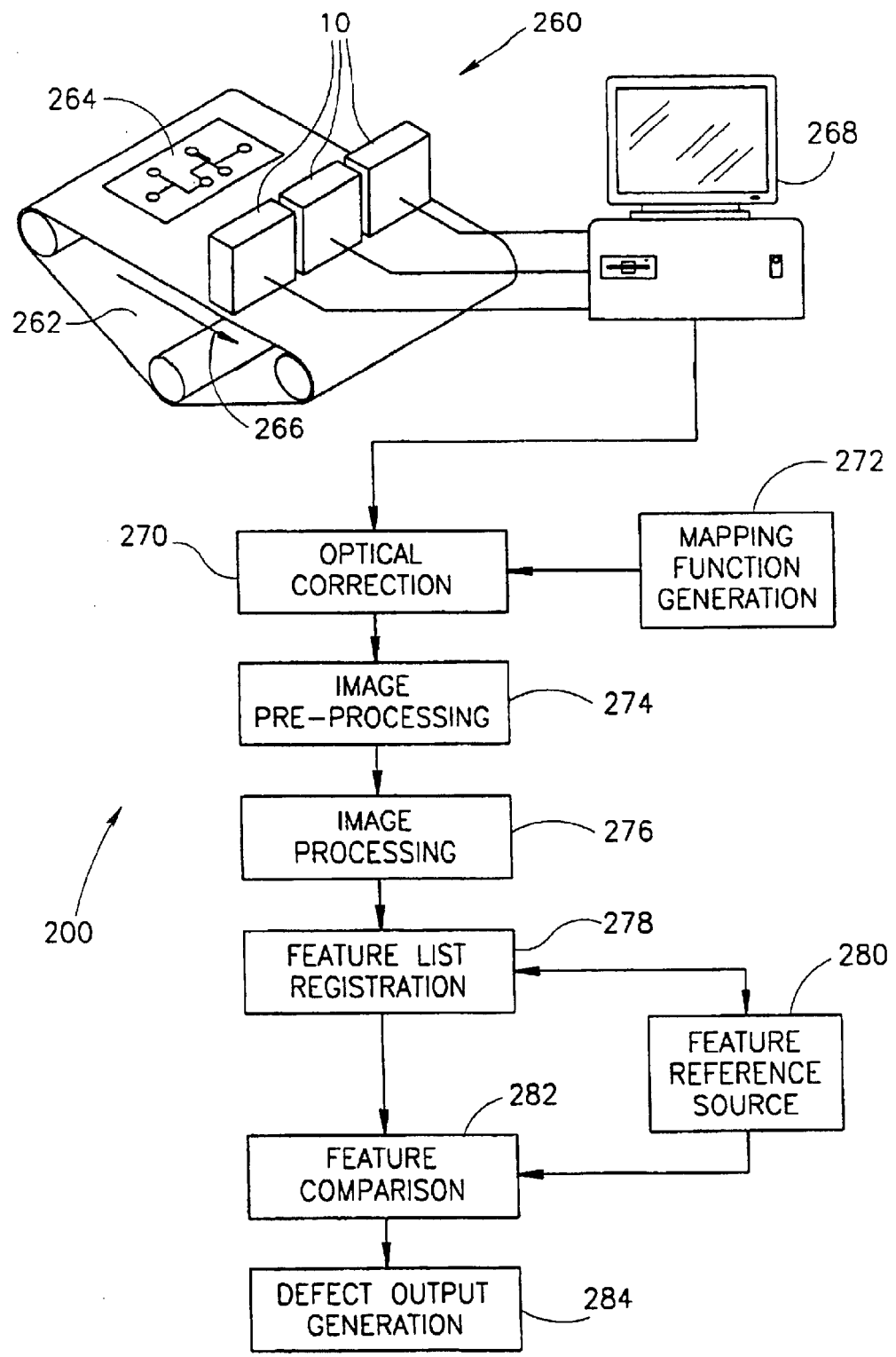
FIG. 6 is a block diagram illustration of a printed circuit board inspection machine including the illumination system of this invention.

A block diagram illustration of a system for the inspection of printed circuit boards (PCBs) preferably implementing an illuminator constructed in accordance with a preferred embodiment of the illuminator is shown in FIG. 6.

An inspection system 200, shown in FIG. 6, comprises an optical array 260 comprising a plurality of illuminators 10 each with their respective collecting optics 24 (FIG. 1).

A conveyor 262 is arranged to transport workpieces, such as PCBs 264, to be inspected past optical array 260 in a transport direction indicated by an arrow 266. A suitable conveyor for use in a preferred embodiment is described in U.S. patent application Ser. No. 09/010,582 and EP Patent application 97300521.8, the disclosures of which is incorporated herein by reference. Inputs comprising a sequence of optical images of strips of the PCB 264 scanned as it passes under optical array 260 are transferred to a computer 268.

In a preferred embodiment of the invention, optical array 260 is comprised of three illuminator units 10, each unit including separate collecting optics 24 (FIG. 1). Each of CCD lines 25–27 comprises a discontinuous line of detectors. The separate collector optics image a linear segment of the workpiece surface onto one of the sections of line detectors 25–27. Preferably the respective fields of view of the collector optics overlap somewhat so that the sections may be referenced to each other or more preferably joined into a complete image of the workpiece. The combined fields of view of the collector optics preferably extend across substantially the entire width of conveyor 260.

Furthermore, it will be noted that in a preferred embodiment of the invention, the three CCD lines 25, 26 and 27 each represent Red, Green and Blue color spectrums respectively, and are offset such that they image slightly offset lines on the illuminated portion of the workpiece. Thus as the workpiece moves beneath the illuminating source, the images acquired by the lines of detectors will be offset by the spacing of the lines of detectors. In accordance with preferred embodiments of the invention, these multi-color images, as well as the relative offsets of the collector optics, are realigned by computer processing, which takes into account both the spacing of lines 25, 26 and 27 and the velocity of PCB 264.

Image reconstruction and subsequent processing is performed by computer 268. Optical Correction Circuitry 270 is provided to reconstruct an image of the inspected PCB and compensate for optical aberrations in acquired images. In a process, typically performed periodically, an inspection test is conducted on system 200 using a test pattern of known configuration. The results from scanning the test pattern are processed to determine optical aberrations, preferably including the respective spatial alignment of images acquired from optical arrays 260, image overlap, differences in accumulation times and the like. Necessary corrections are computed off-line and the results are stored in a Mapping Function Generator. 272 During on-line inspection, optical correction data stored in the Mapping Function Generator 272 is supplied Optical Correction Circuitry 270 and used to effect optical correction of the images acquired from optical array 260 and to reconstruct an optically corrected image of the inspected PCB.

Optical Correction Circuitry 270 provides a corrected sensor array output to Image Pre-Processing Circuitry 274. Image Pre-Processing Circuitry 274 preferably provides a segmentation output indication dividing all areas on the image represented by the corrected sensor array output into categories. For example, in the case of PCBs, every location on the image represented by the corrected sensor array output is identified by the segmentation output indication as being either laminate or conductor. Additionally, Image Pre-Processing circuitry 274 may provide a separate segmentation information based on predetermined gray-scale thresholds in certain color spectra, for example thereby additionally segmenting regions suspected of being oxidized or non-oxidized copper.

A segmentation output indication from Image Pre-Processing Circuitry 274 is supplied to Image Processing Circuitry 276. Image Processing Circuitry 276 provides an image processing output which identifies various features of the image on the PCB and their respective locations. In the case of printed circuit boards, the features are typically pads, conductor junctions and conductive paths, vias and the like, as well as indications of their width, shorts and discontinuities therein. Image Processing Circuitry is preferably a morphology based system, but may alternatively be bit map, net list, design rule or contour based, or based on any other suitable input or combination of the above.

An image processing output of Image Processing Circuitry 276 is supplied to Feature List Registration Circuitry 278, which maps the coordinate system of the output of Image Processing circuitry 276 onto a reference coordinate system. This registration mapping may be tuned dynamically using dynamic registration methods known in the art in accordance with information supplied by a Feature Reference Source 280, such as, for example, that described in U.S. Pat. No. 5,495,535.

An output of Feature List Registration circuitry 278 and an output of Feature Reference Source 280 are supplied to Feature Comparison Circuitry 282, which circuitry compares the now registered map of output of Image Processing Circuitry with a reference stored in Feature Reference Source 280 and provides an output indication of defects. Such defects, in the context of printed circuit board inspection, may typically include absence of required features, the existence of unnecessary features, shorts or discontinuities in connectors, incorrectly shaped features, oxidation and the like defects. An output of the Feature Comparison Circuitry 282 is supplied to a Defect Output Generator Circuitry 284 that prepares a report of defects found on the PCB, which may then be used to assist in manually inspection of defective regions on the PCB. As appropriate, defective PCBs may be repaired or discarded.

While certain features of inspection system 200 have been indicated as being performed by hardware, it should be understood that such features may be performed by software, firmware or combinations of the software and firmware. Furthermore, the functions may be performed utilizing combinations of software, firmware and dedicated hardware.

While the invention has been described with reference to certain preferred embodiments, various modifications will be readily apparent to and may be readily accomplished be persons skilled in the art without departing from the spirit and the scope of the above teachings. In particular, certain embodiments of the invention may not have all of the features of the above described embodiments and further some embodiments of the invention may combine features described above with reference to different embodiments of the invention. Therefore, it is understood that the invention may be practiced other than as specifically described herein without departing from the scope of the following claims:

What is claimed is:

1. Illuminator apparatus for illuminating a workpiece during visual testing thereof, the illuminator comprising:
   a first illumination source arranged to direct light onto a portion of the workpiece from a wedge shaped sector of directions, centered at an illumination axis;
   a second illumination source arranged to direct light onto said portion from two angular sectors, said two angular sectors being separated by said wedge shaped sector;
   an optical viewing system, arranged to view said portion of the workpiece and accept light reflected from the workpiece over a range of angular directions,
   wherein said first and second illumination sources have separately adjustable intensities and said second illumination source comprises a same source for providing said illumination for said two angular sectors.

2. Apparatus according to claim 1 wherein the wedge shaped sector and the two angular sectors form a contiguous illumination sector.

3. Apparatus according to claim 1 wherein the range of angles encompassed by the illumination from the wedge shaped sector and the two angular sectors is substantially less than a total range of 180°.

4. Apparatus according to claim 3 wherein the illumination is arranged to illuminate the workpiece from angles ranging over substantially less than a total range of 100°.

5. Apparatus according to claim 1 wherein the optical viewing system views the portion over a range of viewing angles, centered at a viewing axis, the viewing axis being at an angle offset from said illumination axis.

6. Apparatus according to claim 1 wherein the range of angles encompassed by the illumination from the wedge shaped sector and the two angular sectors is centered at the illumination axis.

7. Apparatus according to claim 1 including a mirror from which the first source is reflected to illuminate the workpiece.

8. Apparatus according to claim 7 wherein the mirror has an extent and the second source is situated behind the mirror such that the mirror blocks illumination therefrom from illuminating the workpiece and wherein said off-axis illumination is comprised of illumination from the second source which passes the mirror outside its extent.

9. Apparatus according to claim 7 wherein the mirror is mounted on a transparent substrate having an extent greater than the extent of the mirror.

10. Apparatus according to claim 7 wherein the first source and the second source are substantially optically equidistant from the minor.

11. Apparatus according to claim 7 and including a concentrating mirror arranged to receive illumination from the first and second sources and concentrate the illumination onto the workpiece.

12. Apparatus according to claim 11 wherein the concentrating mirror comprises an elliptical mirror portion.

13. Apparatus according to claim 12 wherein the first and second sources are optically situated substantially at a focus of the elliptical mirror.

14. Apparatus according to claim 11 wherein the concentrating mirror comprises a base having the general shape of the mirror and a metal foil adhered to the base.

15. Apparatus according to claim 14 wherein the metal foil is adhered to the base by a vacuum applied to the metal foil.

16. Apparatus according to claim 11 wherein the workpiece is situated substantially at a second focus of the elliptical minor.

17. Apparatus according to claim 1 wherein the first source and the second source are line sources.

18. Apparatus according to claim 17 wherein at least one of the first and second line sources is comprised of a plurality of sources that extend along a line.

19. Apparatus according to claim 17 wherein the line source comprises a at least one radiant source and a diffuser through which light that illuminates the workpiece from said source passes.

20. Apparatus for visual inspection of a workpiece comprising:
   illumination apparatus according to claim 1; and
   an optical sensor so situated that it receives light from the optical viewing system and operative produce image signals in response thereto.

21. Apparatus according to claim 20 wherein the illumination apparatus include:
   a transporter operative to move the workpiece relative to the illumination apparatus such that the optical sensor produces image signals representative of successive portions of the workpiece.

22. Apparatus according to claim 1 wherein the on-axis illumination illuminates the workpiece from a range of directions having an angular extent of between about 4° and about 8°.

23. Apparatus according to claim 22 wherein the angular extent of the on-axis illumination is about 6°.

24. Apparatus according to claim 1 wherein the on-axis and off-axis illumination illuminate the workpiece from a range of directions having an angular extent of between 30° and about 60°.

25. Apparatus according to claim 24 wherein the angular extent of the on-axis and off-axis illumination is between about 39° and 45°.

26. Apparatus according to claim 1 wherein the workpiece comprises a printed circuit board.

* * * * *